United States Patent [19]
AEgidius

[11] Patent Number: 5,798,221
[45] Date of Patent: Aug. 25, 1998

[54] METHOD FOR THE CONDITIONING OF LIQUID SAMPLES

[75] Inventor: Poul Erik AEgidius, Helsinge, Denmark

[73] Assignee: Foss Electric A/S, Hillerod, Denmark

[21] Appl. No.: 714,140

[22] PCT Filed: Mar. 16, 1995

[86] PCT No.: PCT/DK95/00119

§ 371 Date: Sep. 16, 1996

§ 102(e) Date: Sep. 16, 1996

[87] PCT Pub. No.: WO95/25174

PCT Pub. Date: Sep. 21, 1995

[30] Foreign Application Priority Data

Mar. 16, 1994 [DK] Denmark .................. 0312/94

[51] Int. Cl.$^6$ .............. C12Q 1/37; C12Q 1/02; C12Q 1/04; G01N 33/53; A23C 9/12
[52] U.S. Cl. .............. 435/23; 435/18; 435/24; 435/29; 435/34; 435/6; 435/968; 435/183; 435/874; 435/876; 435/4; 252/301.16; 436/13; 436/71; 436/800; 437/16; 422/50; 422/55; 426/34; 426/330; 426/33; 426/601; 426/417
[58] Field of Search .............. 435/23, 18, 24, 435/968, 29, 34, 6, 183, 4, 874, 876; 252/301.16; 436/13, 71, 800; 422/50, 55; 426/34, 330, 33, 601, 417; 437/16

[56] References Cited

U.S. PATENT DOCUMENTS 5,256,532  10/1993  Melnicoff et al. .................. 436/71
5,375,606  12/1994  Slezak et al. .................. 128/691

FOREIGN PATENT DOCUMENTS 68654  9/1984  Finland.

*Primary Examiner*—Louise N. Leary
*Attorney, Agent, or Firm*—Birch, Stewart, Kolasch & Birch, LLP

[57] ABSTRACT

A method is disclosed for conditioning samples (of e.g. milk or meat) containing fat globules and somatic cells and/or protein particles before they are subjected to fluorescence measurements in order to determine the bacterial content, as well as methods for performing the determination of bacterial content in such samples. The conditioning method involves the treatment of the samples with an ion-chelating agent, a proteolytic enzyme, detergent, and a bacteriologically specific fluorochrome such as ethidium bromide. Detergent is used in a concentration resulting in substantially no dissolution of the fat globules and the conditioned samples thus loses insignificant amounts of fat globules. The assessment of fluorescence is preferably performed in a conventional flow cytometer. As no separation of fat globules is necessary, the methods are simple and fast. The bacterial determinations have proved reliable when compared to standard methods.

48 Claims, 4 Drawing Sheets

METHOD FOR THE CONDITIONING OF LIQUID SAMPLES

The present invention relates to a novel method for conditioning a liquid sample, such as a milk sample, for determining the amount of bacteria therein by fluorescence determination, in particular by flow cytometry, as well as a method for performing the determination.

It is known to determine the number of bacteria in milk by staining with a fluorochrome, irradiating with light in a waveband in which the fluorochrome absorbs, and assessing the resulting fluorescence.

Thus, EP-A 8826, published on 19 Mar. 1980, discloses a method for counting bacteria in a bacteria-containing liquid sample, such as milk. Prior to the counting procedure, the milk is subjected to lysis of somatic cells by means of EDTA and centrifugation to isolate the bacteria from the other components of the sample (that is, fat globules and somatic cell walls), and the suspension of bacteria so isolated is treated with a proteolytic enzyme such as subtilisin, and stained with a combination of a fluorochrome, in particular acridine orange, EDTA, and a detergent. After this staining of the isolated bacteria, the bacterial suspension is applied as a thin film on the outer rim of a rotating disc, the film is subjected to irradiation, and the light signals emitted from the stained bacteria are used as the basis for determining the number of bacteria in the sample.

In recent years, attempts have been made to perform determination of bacteria in milk using simpler and faster techniques, in particular flow cytometry.

Thus, FI published patent specification No. 68654, published on 9 Sep. 1984, discloses a method in which the amount of somatic cells and bacteria in natural suspensions such as milk is measured by homogenizing at 45°–55° C., adding a phosphate buffer, pH 7.4, containing 20–100 μg of ethidium bromide per ml buffer, and subjecting the resulting suspension to fluorescence determination in a flow cytometer.

A more recent strategy, suggested in EP-A 342501, published on 9 May 1988, comprises treating the milk with a clarification reagent essentially consisting of a non-ionic detergent, a $C_{1-8}$ alcohol and a buffer of pH more than 10, and a colour reagent such as ethidium bromide, and excitation and fluorescence determination in a flow cytometer. The clarification will selectively break down the non-cellular particles contained in the milk without affecting any microbial or somatic cells which may be present.

Thus, the strategies suggested in the art comprise measurement of both somatic cells and bacteria, the most recent strategy involving removal of fat globules prior to such measurement.

In connection with comprehensive research leading to the present invention, it has been found that to obtain signal to noise ratios in flow cytometry fluorescence assessment which will ensure reliable results which are in agreement with accepted standard techniques (Standard Plate Count), it is necessary to degrade and solubilize the casein micelles/particles which are inherently present in milk, as the presence of casein has a tendency to lead to precipitation of protein and formation of protein coatings in the apparatus employed. It has also been found that the means available for the degradation of casein, i.e. proteolytic enzymes, as well as those available for staining of the bacteria, i.e. bacteriologically specific fluorochromes, will give rise to a certain degradation of the somatic cells, resulting in cell debris which will impair the signal to noise ratio, which means that the somatic cells must be lysed, degraded and solubilized, contrary to the teaching of the two above-mentioned patent applications relating to flow cytometry. On the other hand, it has also been found that contrary to the most recent of the above-mentioned patent applications and contrary to the teaching of EP-A 8826, it is possible to obtain a satisfactory signal to noise ratio in the fluorescence assessment without removing the fat globules, thereby very considerably simplifying the sample conditioning and the instrumentation used.

The present invention is based on these recognitions and relates to a method for preparing a conditioned sample from an initial liquid sample containing 1) fat globules and
2) somatic cells and/or protein particles, the method comprising treating the initial sample with
   an ion-chelating agent,
   a proteolytic enzyme,
   a detergent, and
   a bacteriologically specific fluorochrome so as to lyse the somatic cells and degrade and solubilize the protein particles and the cell debris from the somatic cells and stain substantially all bacteria in the initial sample, the detergent being used in a concentration at or below the maximum concentration at which substantially no dissolution of the fat globules will take place, and thereby obtaining the conditioned sample which contains substantially the same amount of intact fat globules but a substantially lower amount of intact somatic cells and intact protein particles than does the initial sample.

In the present context, the term "conditioning" means making the sample ready for the determination of the concentration or number of bacteria in a sample by a fluorescence technique. The term "a fluorescence technique" designates any technique in which the sample is irradiated with light in a waveband in which the fluorochrome absorbs, and the resulting emitted fluorescence is determined, either visually, by means of computerized image analysis, or by means of a suitable transducer such as a photo multiplier or a photo diode. The term "lyse", as used in connection with somatic cells, indicates rupturing the cell walls of the somatic cells, leaving cell debris. The term "degrade and solubilize", as used in connection with protein particles and cell debris, indicates decomposition of the protein particles and the cell debris, e.g., by hydrolysis of proteins, to result in particles or molecules which are so small that the fluorescence generated by the fluorochrome bound to the particles or molecules does not to any substantial extent generate fluorescence peaks not distinguishable from the fluorescence peaks generated by the fluorochrome-stained bacteria and thus does not disturb the assessment in the above-mentioned fluorescence techniques. The fluorescence emitted from a particle or molecule normally depends more on the amount of fluorophore bound thereto than on the size of the particle or molecule in question. This is related to the fact that the fluorochrome preferably used stains DNA or RNA, which is present in varying amounts in the particles or molecules present in the sample subsequent to degradation and solubilisation.

According to an important embodiment of the invention, it has been found while the efficiency and selectivity of the staining are considerably enhanced when the initial sample is treated with the fluorochrome in the presence of a detergent, the beneficial effect of the detergent is obtained only when the detergent is used in an amount below a certain critical limit: when this critical limit is exceeded, the efficiency of the staining of the bacteria is dramatically reduced, thus seriously decreasing the signal/noise ratio in the later fluorescence measurement. While this critical amount will, of course, vary to some extent depending on the type and identity of the detergent, a practical upper limit, substantially independent of the type and identity of the detergent, has been found to be the maximum concentration of the detergent at which substantially no dissolution of the fat globules will take place.

In the present specification and claims, the phrase "substantially no dissolution of fat globules" indicates that only an insignificant clarification of the initial sample (of e.g. milk) is performed. A quantitative assay for the dissolution of fat globules is the following: An initial sample is divided into two aliquots of which the first is conditioned according to the invention whereas the second (the control) is diluted equivalently in an inert solvent, e.g. distilled water. Both samples are irradiated with light which is scattered by the fat globules (e.g. light at a wavelength of 488 nm), and the intensity of scattered light at an angle of 90° to the irradiating light is assessed. A conditioned sample wherein substantially no dissolution of fat globules have taken place is herein defined as one which results in an intensity of scattered light which is at least 50% of the intensity measured from the control. It is preferred that the intensity of scattered light from a conditioned sample is at least 60%, more preferably 70%, and most preferably at least 80% of a control sample as defined above.

The initial sample may be treated sequentially with the detergent, the chelating agent, the enzyme, and the fluorochrome in any sequence. However, the following strategies are of particular interest:

1) The initial sample is first treated with the chelating agent, then with the enzyme, then with the detergent, and then with the fluorochrome.

In this manner, the somatic cells are lysed and the protein particles/micelles are partly disintegrated by the treatment with the chelating agent, thereby improving the efficiency of the proteolytic enzyme in the digestion of the protein particles/micelles, and then the detergent further solubilizes cell debris and/or enhances the staining of the bacteria.

2) The initial sample is first treated with a combination of the chelating agent and the enzyme, then with the detergent, and then with the fluorochrome.

In this manner, the disintegration is performed simultaneously with the digestion of the protein particles, thereby saving an operation step without sacrificing the advantages of the beneficial sequence.

3) The initial sample is first treated with a combination of the chelating agent, the enzyme, and the detergent, and then with the fluorochrome.

In this manner, the total preparation of the sample for the staining is performed in one efficient step, whereupon the fluorochrome is added to the thus prepared sample, in which case the staining step may be performed during a very short incubation, down to 2 seconds, but normally 5 seconds or 10 or 20 seconds, whereby the fluorochrome may be added as a solution in a buffer, such as a phosphate buffer, different from the normally alkaline buffer used in connection with the other ingredients, or as a solution in purified water. Thereby, the stability of alkaline-sensitive fluorochromes is improved compared to the situation where the fluorochrome is dissolved in an alkaline buffer.

4) The initial sample is treated with a combination of the chelating agent, the enzyme, the detergent, and the fluorochrome.

This embodiment, which preferably uses a fluorochrome, such as ethidium bromide, the stability of which is not particularly alkaline-sensitive, will, of course, constitute the simplest and fastest approach from the point of view of operational stages.

At least as far as the treatment steps involving treatment with the enzyme are concerned, a certain minimum incubation time is preferably used, such as an incubation time of at least 0.5 minutes. Preferably, the incubation time is in the range of 0.5–20 minutes. The selection of the incubation time for the treatment with the enzyme will be made on the basis of the total enzyme activity; normally, the necessary incubation time is reversely proportional to the enzyme concentration. In order to obtain the maximum capacity, the incubation time will normally be selected as the shortest possible incubation time which is found to ensure results conforming with standard methods. Similar considerations apply to the incubation (staining) with the fluorochrome.

The temperature of the sample being treated with the enzyme or with the bacteriologically specific fluorochrome is preferably in the range of 15°–80° C. and, within this range, is suitably adapted to the temperature optimum of the enzyme or bacteriologically specific fluorochrome used and to the practical liquid/mechanical handling of the sample.

The pH of the sample being treated is preferably kept in the range of 6–11, as most of the enzymes optimally suited for the purpose (see further below) have their pH optima in this range, and as an alkaline pH will tend to solubilize casein. The pH is suitably kept in the range in question by means of a buffer, in particular a buffer selected from the group consisting of:

Phosphate (pH 5.0–8.0) (see Sørensen, S. P. L., Biochem. Z., 21, 131, (1909), and 22, 352 (1909); Ergebn. Physiol., 12, 393 (1912); Walbum, L. E., Biochem. Z., 107, 219 (1920)).

Sodium borate/HCl (pH 7.8–9.2) (see Sørensen, S. P. L., Biochem. Z., 21, 131, (1909), and 22, 352 (1909); Ergebn. Physiol., 12, 393 (1912); Walbum, L. E., Biochem. Z., 107, 219 (1920)).

Glycine/NaOH (pH 8.6–12.8) (see Sørensen, S. P. L., Biochem. Z., 21, 131, (1909), and 22, 352 (1909); Ergebn. Physiol., 12, 393 (1912); Walbum, L. E., Biochem. Z., 107, 219 (1920)).

Sodium borate/NaOH (pH 9.4–10.6) (see Sørensen, S. P. L., Biochem. Z., 21, 131, (1909), and 22, 352 (1909); Ergebn. Physiol., 12, 393 (1912); Walbum, L. E., Biochem. Z., 107, 219 (1920)).

Barbital-Na/HCl (pH 7.0–9.0) (See Michaelis, L., J. biol. Chem., 87, 33 (1930)).

Piperazine/HCl (pH 8.8–10.6) (See Smith and Smith, Biol. Bull., 96, 233 (1949); Semenza et al., Helv. chim. Acta, 45, 2306 (1962)).

Tetraethylethylenediamine (pH 8.2–10.0) (See Semenza et al., Helv. chim. Acta, 45, 2306 (1962)).

Trismaleate (pH 5.2–8.6) (See Gomori, G., in Colowick and Kaplan (Eds.), Methods in Enzymology, vol. 1, Academic Press, New York, 1955, page 138; Gomori, G., Proc Soc. exp. Biol. (N.Y.), 68, 354, (1948)).

Dimethylaminoethylamine (pH 5.6–7.4 and 8.6–10.4) (See Semenza et al., Helv. chim. Acta, 45, 2306 (1962)).

Triethanolamine/HCl (pH 7.0–8.8) (See Beisenherz et al., Z. Naturforsch., 8b, 555 (1953)).

N-Dimethylaminoleucylglycine/NaOH (pH 7.0–8.8) (See Leonis, J., C. R. Lab. Carlsberg, Ser. Chim., 26, 357 (1948)).

Tris/HCl (pH 7.2–9.0) (See Gomori, G., in Colowick and Kaplan (Eds.), Methods in Enzymology, vol. 1, Academic Press, New York, 1955, page 138).

2-Amino-2-methylpropane-1,3-diol/HCL (pH 7.8–10.0) (See Gomori, G., in Colowick and Kaplan (Eds.), Methods in Enzymology, vol. 1, Academic Press, New York, 1955, page 138; Gomori, G., Proc. Soc. exp. Biol. (N.Y.), 68, 354, (1948)), and Carbonate (pH 9.2–10.8) (See Gomori, G., in Colowick and Kaplan (Eds.), Methods in Enzymology, vol. 1, Academic Press, New York, 1955, page 138; Delory and King, Biochem. J., 39, 245 (1945)).

The preferred chelating agent is a calcium-chelating agent, such as a chelating agent selected from the group consisting of the following chelating agents, or a salt thereof:

All BAPTA (1,2-Bis(2-Aminophenoxy)Ethane-N,N,N',N'-Tetraacetic Acid)-like chelators (See "New Calcium Indicators . . . " R. Y. Tsien, Biochemistry 19, 2396 (1980); "On the Dissociation Constants of . . . " R., Pethig, et al. Cell Calcium 10, 491 (1989); "Synthesis and Characterization . . . " L. A. Levy, E. Murphy, R. E. London. Am. J. Physiol. 252, C441 (1987)), EDTA ([Ethylenedinitrilo ]tetraacetic Acid), EGTA (Ethylene glycol-bis(β-aminoethyl Ether) N,N,N',N',-Tetraacetic Acid), APTRA (2-aminophenol-N,N,O-triacetic acid, tripotassium salt) and related derivatives (See Biochemistry 27, 4041 (1988); T. Meyer and L. Stryer in Annual Review of Biophysics and Biophysical Chemistry, Vol 20; D. M. Englemann, Ed., Annual Reviews (1991) pp. 153–174), and DTPA (N,N-bis[2-(bis[Carboxymethyl]amino)ethyl] glycine; Penteic acid) (See "Kinetics of Calcium . . . " T. Meyer, T. Wensel, L. Stryer. Biochemistry 29, 32 (1990); "Highly cooperative . . . " T. Meyer, D. Holowka, L. Stryer. Science 240, 653 (1988)).

According to one important feature of the invention, it has been found, on the one hand, that the ion-chelating agent improves the stainability of the bacteria, but, on the other hand, that there is a maximum concentration of the ion-chelating agent at which it will start to have an adverse effect on the stainability. Thus, with reference to an easy and reproducible test which can be used to determine the maximum preferable concentration of the ion-chelating agent, the ion-chelating agent is preferably used in a concentration of about at or below the concentration at which an increase of the concentration will result in a decrease of the stainability of an overnight culture of *Pseudomonas fluorescens* adjusted to optical density 0.5 at 620 nm, in phosphate buffer, pH 7.4, with ethidium bromide in a concentration of 2 µg per ml in the presence of 0.05 vol/vol % Brij 96, as measured by flow cytometric fluorescence assessment.

Subject to the above considerations, the ion-chelating agent will normally be used in a concentration of about 1–10 g per liter, preferably about 2–5 g per liter.

As examples of suitable proteolytic enzymes may be mentioned enzymes classified class 3.4 (peptide hydrolases) in the international enzyme nomenclature system of 1972, in particular in the subclasses 3.4.22 (thiol proteinases), 3.4.24 (metalloproteinases), and 3.4.99 (proteinases of unknown catalytic mechanism), and in the subclass to which subtilisin pertains, that is, subclass 3.4.21 (serine proteinases), the enzymes of interest in this class being the ones with broad specificity.

It is preferred that the proteolytic enzyme has its maximum activity in the pH range of 6 to 11. An enzyme which has been found particularly suitable in praxis is subtilisin.

The proteolytic enzyme is normally used in a concentration of at least 0.02 Anson unit, in particular a concentration of at least 0.05 Anson unit, such as a concentration of about 0.050–0.5 Anson unit, at present preferably a concentration of about 0.08–0.15 Anson unit.

The detergent is suitably a so-called biological detergent, that is, a detergent of a type known to be effective for solubilisation of proteins and membrane components, see, e.g., Sigma product catalogue of Biochemicals and Organic Compounds for Research and Diagnostic Reagents, Sigma Chemical Company, St. Louis, Mo., U.S.A., 1992. As examples of suitable detergents may be mentioned nonionic biological detergents such as a polyoxyethylene ether (e.g., a lauryl, oleyl, stearyl or tridecyl ether), e.g. Brij 96, Triton X100, or Triton X165; a polyoxyethylenesorbitan ester, such as monolaurate (Tween 20), monooleate (Tween 80), monopalmitate, monostearate, or trioleate, preferably Tween 80 or Tween 20; or digitonin. Among these, Brij-96 and Tween 80 are presently preferred.

The detergent is normally used in an amount of between 0.01 and 2 per cent by volume, with the proviso that the concentration used will, of course, be at or below the maximum concentration at which substantially no dissolution of the fat globules will take place, in accordance with what is stated above. The detergent is presently preferably used in an amount of 0.03–0.1 per cent by volume, with the above proviso.

For most purposes, a practical guideline for selecting the concentration and combination of the chelating agent and the detergent, is to use such chelating agent and such detergent in such concentrations that they are effective to solubilize somatic cells in milk to an extent resulting in at least a 95% decrease in cell count by the AOAC-approved Fossomatic 360 from Foss Electric A/S.

The fluorochrome is selected from DNA/RNA-binding fluorochromes, fluorochromes specifically binding to bacterial cell walls or bacterial flagella, and bacterial viability stains. As an indication of sufficient bacteriological specificity, it is preferred that the fluorochrome is one which, when added in a concentration of 10 µg per ml at room temperature to unhomogenized whole milk having a fat content of 3.5% by weight, the resulting mixture being tumbled gently for 5 minutes, does not give rise to any staining of fat globules which is detectable by fluorescence microscopy on glass slides, using a 50 watt mercury lamp as the radiation source. The above test will, inter alia, exclude the use of acridine orange, a fact which is in good agreement with results obtained in the course of investigating the present invention. Presently preferred fluorochromes are those which belong to the group of phenanthridium derived intercalators, such as propidium iodide or ethidium bromide, both of which will, in addition to the thus assessed property of not staining the fat globules, result in a satisfactory staining of the bacteria.

It is presently preferred that the fluorochrome is ethidium bromide, which is preferably used in a concentration of at least 0.1 µg per ml of the liquid sample, in particular in a concentration of at least 0.5 µg per ml of the liquid sample, such as a concentration of about 1.5–10 µg per ml of the sample.

The most important kind of sample to be subjected to the method of the present invention is a sample of or derived from a food or a feed product, in particular a sample in which the fat globules are milk fat globules, and the presently most important kind of sample is a milk sample. It is however, also possible to employ the methods of the invention in the determination of bacterial counts in other types of samples, i.a. samples of homogenized meat as well as samples of dairy products such as cheese and yoghurt, fresh or processed meat, poultry, seafood, bakery, fermented foods, and salads etc.

After performing a conditioning according to the invention as discussed above the conditioned sample or a part thereof can be subjected to light in a wavelength range exciting the fluorochrome, and the fluorescence emitted can be assessed, and the number of bacteria in the sample can be determined on the basis of the fluorescence. Such a determination of bacteria in an initial sample constitutites another important part of the invention.

The determination of the number of bacteria can be performed in a number of ways. As described herein, it is possible to separately measure the fluorescent emission from each bacterium in a conditioned sample (by using the methods described herein, e.g. flow cytometry). Thereafter, it is possible to interpolate in standard curves over the relationship between known numbers of bacteria in standard samples and the number of discretely emitted fluorescence impulses from the conditioned samples. In a similar manner, it is also possible to correlate the fluorescence measurements to bacterial numbers determined from the use of a standard protocol from samples of unknown bacterial content. As shown in the example disclosed herein, one method of the invention for determining the number of bacteria in a sample exhibits excellent correlation with two widely accepted standard protocols, and it is thus possible to interpolate from the fluorescence measurement to the bacterial counts and thereby obtain reliable results.

The light exciting the fluorochrome is suitably light from a broad band light source such as a xenon or mercury lamp, but it is also within the scope of the invention to use laser light.

A preferred embodiment of the method of the invention for determining bacterial numbers in a sample is where the fluorescence is measured while the sample or part of the sample is flowing as a liquid string in a flow cytometer.

The heart of a flow cytometer is a flow chamber which receives the sample and forces it at high speed through a beam of exciting light as a thin, linear stream. If the sample contains particles, these will be forced into the stream and each particle will be illuminated for a very short time. When illuminated, the particle will cause an optical event such as scatter of the exciting light at certain angels to the exciting light, absorbtion of the exciting light, or emission of fluorescence.

By arranging suitable optical filters, photomultipliers or photodiodes and transducers around the flow chamber, the optical events can be detected, processed and recorded. The events characterize the particle and hence a specific group of particles in a complex mixture of particles can be identified on the basis of the optical events. If the volume of sample passing the exciting light in the spray is known or can be calculated, then a specific group of particles in a complex mixture can be identified and quantified.

The selectivity of the optical events caused by a particle can be improved by manipulating the chemical composition or properties of the particle. This can e.g. be accomplished by introducing a fluorescent stain with specific affinity towards a particle relevant to the analysis, causing the particle to emit fluorescent radiation when passing the beam of exciting light in the flow chamber.

Although some selectivity is achieved by choice of a stain specific towards a particle relevant to the analysis, the stain is often specific towards a property of the particle (such as DNA content) also present in particles not relevant to the analysis.

The selectivity of the optical events in the flow chamber can be further improved by removing, degrading or digesting particles with properties similar to those of the particle relevant to the analysis. This can be achieved by means of conventional separation technologies (centrifugation) or by enzymatic digestion. As will be clear from the present specification and claims, it is within the scope of the present invention to improve the selectivity of the optical events (improving the signal to noise ratio) by such measures.

It is also within the scope of the invention to use the above mentioned method in which the fluorescence is measured while the sample is applied as a film onto the outer rim portion of a rotating disc, where the film is irradiated with light and where the emitted fluorescence is collected by a microscope objective and transmitted to a transducer, such as disclosed e.g., in the above mentioned EP-A 8826. The application of the rotating disc system disclosed in EP-A 8826 excludes the use of light scatter to characterise a particle relevant to the analysis, because only the optical events 180° to the exciting light path are collected. Such exclusion of an optical event which might characterise the particles of relevance to the analysis, stress the importance of the method of the invention which uses a selective stain and a selective method to remove, degrade or digest other particles which might interfere in the fluorescence measurement.

Finally, according to the invention the amount of bacteria in a sample can be assessed by use of a microscope (by epifluorescence microscopy). The microscope magnifies the image of the particles in the sample and by use of a suitable magnification allows a visual inspection of particles in the sample by the viewer. If the inspected volume is known, the concentration of particles relevant to the analysis can be calculated. Although a visual inspection allows a selection on particles based on both dimension and shape, the selection of particles relevant to the analysis in a complex mixture is often very difficult or impossible to achieve. Some selectivity can be achieved by employing an absorbing stain having affinity towards the particles relevant to the analysis, as applied e.g. in traditional histochemistry. For instance, protein particles can be coloured black with the stain Amido Black. Nevertheless, the particles which are irrelevant to the analysis often remain visible to the viewer.

The selectivity of the particles inspected by the viewer can be further improved by equipping the microscope with an exciting light source and optical filters similar to those used in the flow cytometer and rotating disc described above and by selecting a fluorescent stain specific to the particles relevant to the analysis. Only particles emitting fluorescence will remain visible to the viewer, and the selectivity of optical events discussed above will apply.

Analytical applications of inspection by microscope is often limited by the very small volume inspected at large magnification. To compensate, several inspections are made on a number of random selected volumes of the sample compromising the cadence of the analysis. Further, the selectivity of identifying the particles relevant to the analysis as based on size and shape is often biased by the viewer. Therefore, it is preferred to increase cadence and minimise the bias imposed by the viewer by equipping the microscope with a computer controlled digital image analyzer. In this way, the computer can be instructed to count particles based on a pre-set size and shape criteria by the use of software designed to this purpose, or the computer can use a neural network which has been trained in the recognition of the particles relevant to the analysis. The previously discussed selectivity of the optical events will therefore also apply to an analysis using a microscope equipped with a computer controlled digital analyzer.

While the above description of the invention is intended to be centred around the cases where the fat globules are substantially not removed from or dissolved in neither the initial nor the conditioned sample and, thus, are present during the fluorescence measurement, it will be understood from the above explanation of the advantages of the invention that they do also, at least to some extent, apply in cases where a removal, replacement or dissolution of the fat globules or solvent of the conditioned sample is in fact performed.

The particular advantages of this aspect of the invention reside in the improved sample conditioning obtained using the sequences and combinations stated, and, in particular, the initial treatment with the chelating agent and the enzyme, when performed prior to removal of the fat globules by centrifugation, will result in a further improved signal to noise ratio because centrifugation is more efficient in collecting large particles (the bacteria) than smaller particles (degraded somatic cells), because the small particles have a higher diffusion coefficient. Another advantage is that excess fluorochrome which is not bound to the bacteria but rather dissolved or suspended in the solvent or (to a smaller extent) in the fat globules can be removed prior to the fluorescence determination.

FIG. 1 schematically illustrates a device useful for determining the amount of bacteria in a sample by fluorescence assessment. This device is a flow cytometer of a kind known per se.

Figure 1:
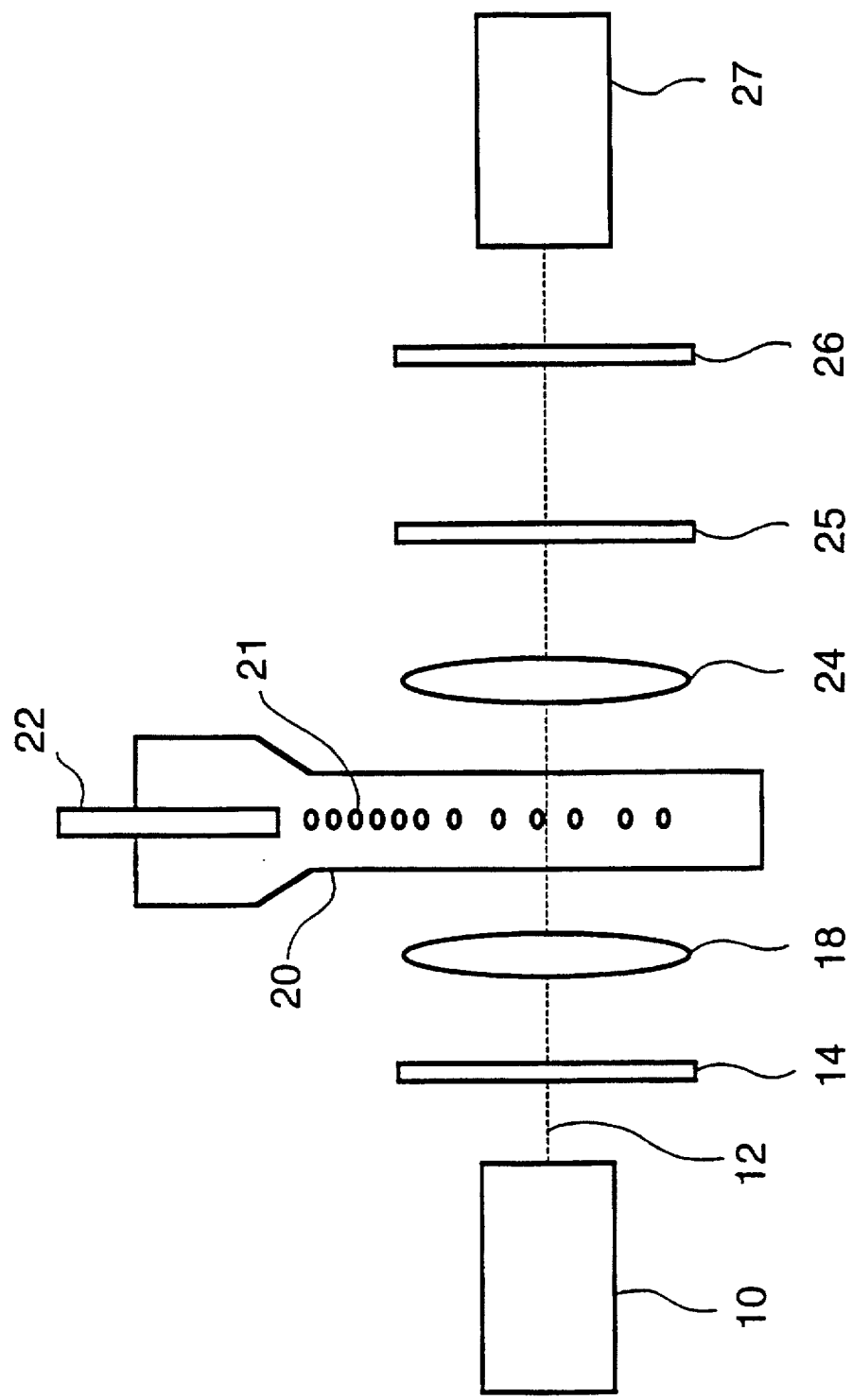

Referring to FIG. 1, a specimen to be assayed, and which has been conditioned as described herein, e.g. in the Example below, is discharged from a nozzle 22. A sheath fluid flows in a laminar flow around the specimen so as to form a sheath flow. Bacteria 21 contained in the sample flow line flow in the centre of a flow cell 20.

A light beam 12 from a broad band light source 10, such as a xenon lamp, is directed through a filter 14, which removes light which is not in the waveband in which the fluorophore absorbs, such as Infra Red (IR) light and light in the waveband in which the fluorophore emits, to the flow cell 20 and focused on to the bacteria 21 by means of a condenser lens 18. This light beam 12 comprises light in a waveband in which the fluorochrome attached to the bacteria absorbs.

The fluorescence from the light-emitting bacteria is collected by a lens 24, transmitted through a filter 25, transmitting the fluorescence from the bacteria, but removing any remaining light in the waveband in which the fluorochrome absorbs, and through a filter 26 transmitting the fluorescence from the bacteria, but removing any IR light emitted by the light source 10, and is focused on to a photo multiplier 27 measuring the fluorescence.

It should be noted that the photo multiplier 27 preferably will be positioned at another position relative to the light beam 12 than depicted in FIG. 1, as the direct light from the excitation source thus can be avoided. In preferred embodiments the photo multiplier 27 will be positioned at 90° relative to the light beam 12 or 180° relative to the light beam 12.

The bacteria will be detected as peaks of fluorescence which may be separated from the background noise by a pulse height analyzer (not shown) which removes detected pulses having a height lower than a certain threshold, whereby the number of detected bacteria will be the total number of pulses exceeding the threshold. When the rate of the flow of the sample in the flow cell 20 (volume per unit of time) is known, the concentration of bacteria in the sample can be determined on the basis of the number of determined fluorescence peaks and the time period in which these peaks have been detected.

EXAMPLE

In this example, a milk sample is treated with a combination of chelating agent, the enzyme, the detergent and the fluorochrome.

Raw milk 43 raw milk samples were collected from farmers tanks. To obtain a homogenous distribution of bacteria the milk is preferably homogenised. This improves the reference method with accordance to estimating the number of colony forming bacteria in the sample as opposed to the number of colony forming units. In this example the milk has been homogenised on a Polytron, from Kinematica, at step 6 for 10 seconds.

Reagent

The reagent contains:

1) $Na_2CO_3$ 7.60 g/l
2) $NaHCO_3$ 8.84 g/l
3) $Na_2H_2EDTA.H_2O$ 2.43 g/l
4) $Na_4EDTA.4H_2O$ 2.71 g/l
5) Subtilisin A (Novo) 91.2 mUnit/l
6) Ethidium Bromide 5.0 mg/l The ingredients 1) through 6) are added to purified water and filtered through a 0.22 μm filter. The pH is controlled to be in the range 9.3 to 9.5. For practical handling purposes ingredient 1 through 4 may be prepared in purified water as a stock buffer solution at 2 times the concentrations stated above. Reagent 6 may be prepared in a fluorochrome stock solution containing 1 g/l.

Reagent 5 is supplied as an enzyme-stock-solution containing 2.4 Unit/l.

The reagent is prepared from the stock-solutions by mixing:

500 ml buffer-stock-solution, 5 ml fluorochrome stock solution, 38 ml enzyme stock solution, and adding water to 1000 ml.

Reference method

The reference method is performed on the milk samples in accordance with International Dairy Federation standard 100b.

BactoScan 8000 method

The BactoScan 8000 method is performed on the milk samples according to the manufactures procedure (Foss Electric, Denmark). The method is e.g. in Germany approved as a routine method for determination of the concentration of bacteria in milk.

Conditioning the sample 4 ml of the above described reagent is added to 1 ml of milk which is then agitated and incubated at 50° C. for 5 minutes.

Analysing the conditioned sample

Figure 2:
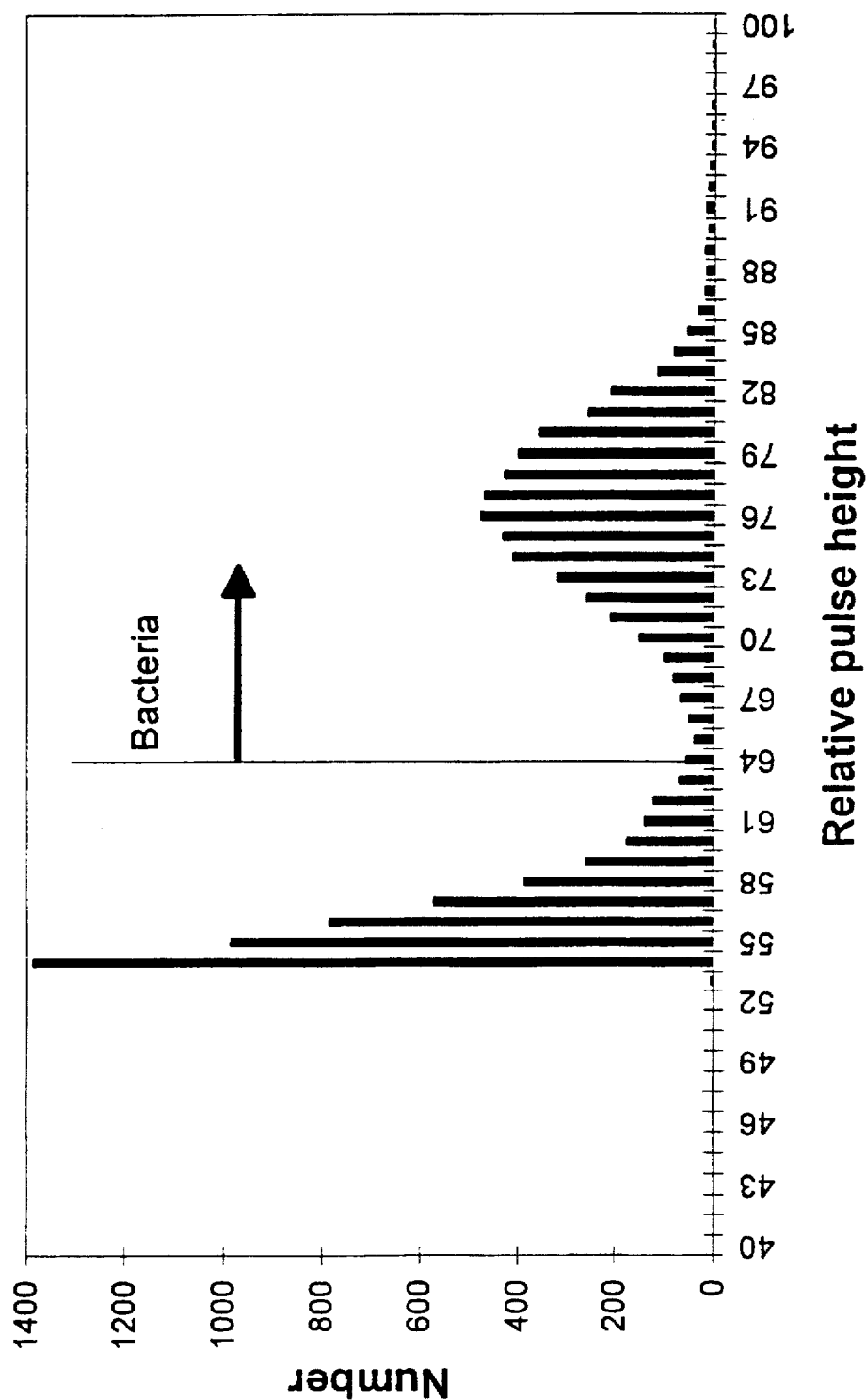
FIG. 2 is a pulse height diagram generated on a FACScan® flow cytometer.

The conditioned sample is fed into a FACScan® flow cytometer. The fluorescence is detected and a pulse height analysis diagram is generated (FIG. 2). From this pulse height diagram, in which the stained bacteria forms peaks which are easily distinguishable from the background noise, the individual bacteria may be detected and counted. By relating the flow volume of sample flowing through the flow cytometer to the total number of detected bacteria (signals exceeding the noise-signals), the concentration of bacteria in the sample may be determined.

Results

A good signal to noise ratio was confirmed on the FacScan® flow cytometer from Becton Dickinson, using the recommended sheath fluid for this instrument (see FIG. 2).

Figure 3:
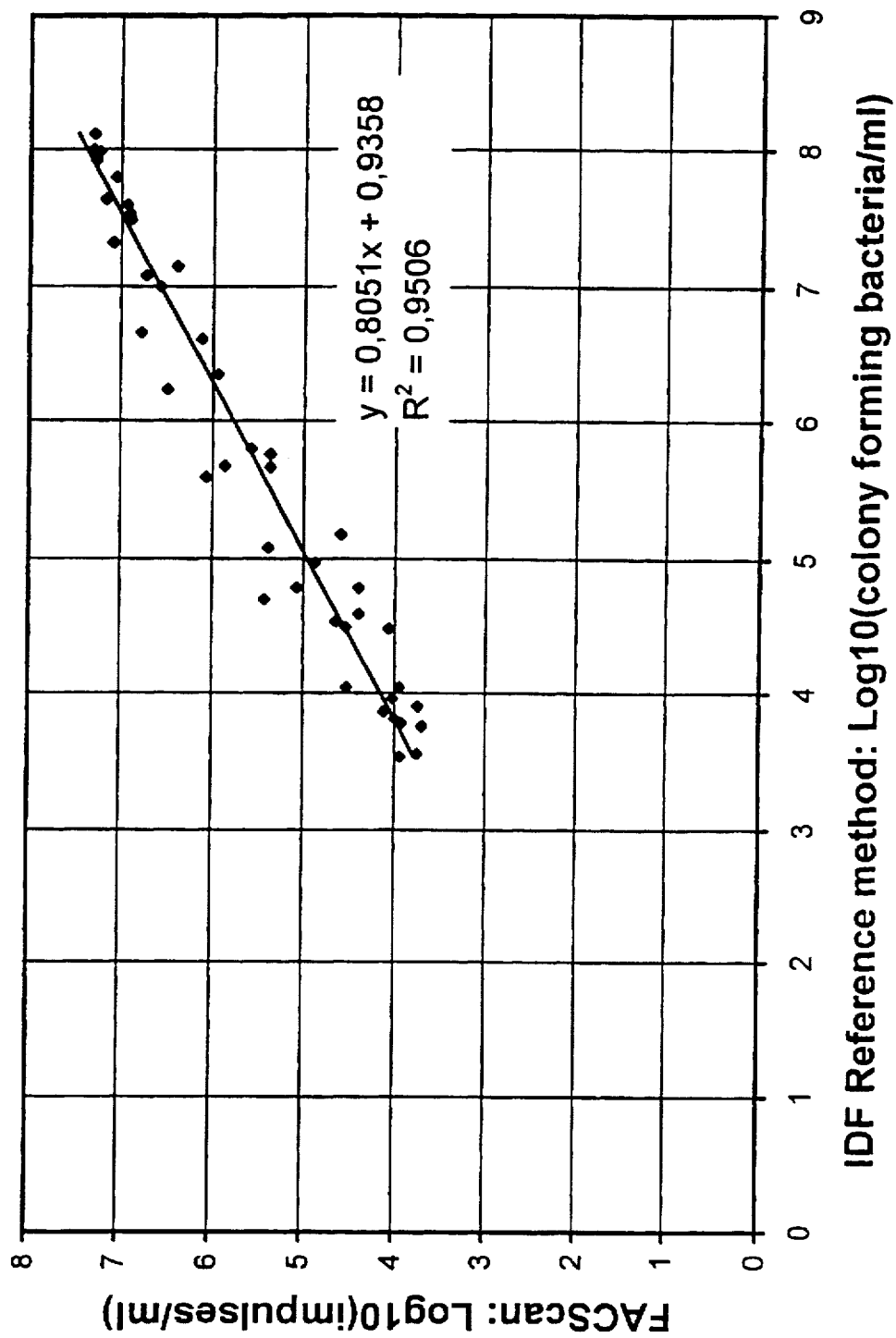
FIG. 3 is a graph showing the log10(impulses pr ml) collected from the FACScan® versus log10(colony forming bacteria) by the reference method.
Figure 4:
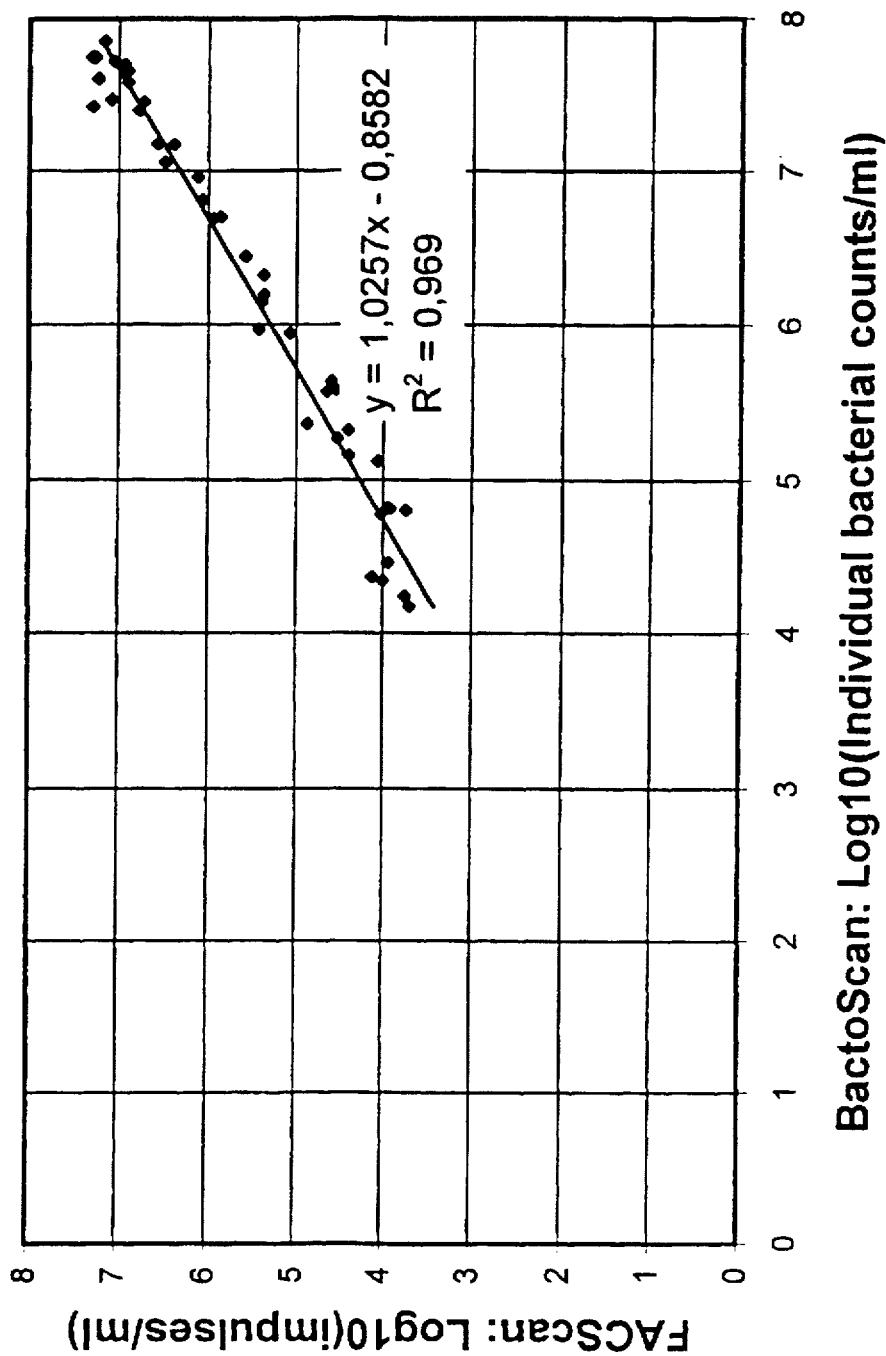
FIG. 4 is a graph showing log10 (impulses pr ml) collected from the FACScan® versus log10 (Individual bacterial counts) by the BactoScan 8000 method.

Further, the number of fluorescence impulses from raw milk conditioned as described above and determined in an experimental setup using the principle illustrated in FIG. 1 exhibited excellent correlation with both the reference method (cf. FIG. 3, $R^2=0.9506$) and with the BactoScan 8000 method (cf. FIG. 4, $R^2=0.969$). This is evidence of the reliability of the methods of the invention and renders probable the future use of these novel methods as fast, simple and reliable alternatives to the present standard protocols for the determination of bacteria in e.g. milk samples.

I claim:

1. A method for preparing a conditioned sample from an initial liquid sample, said initial liquid sample containing fat globules and somatic cells and/or protein particles, the method comprising treating the initial sample with an ion-chelating agent, a proteolytic enzyme, a detergent, and a bacteriologically specific fluorochrome so as to lyse the somatic cells and degrade and solubilize the protein particles and the cell debris from the somatic cells and stain substantially all bacteria in the initial sample, wherein said detergent is used in a concentration at or below the maximum concentration at which substantially no dissolution of the fat globules will take place, and thereby obtaining the conditioned sample which contains substantially the same amount of intact fat globules but a substantially lower amount of intact somatic cells and intact protein particles than does the initial sample.

2. The method according to claim 1, wherein the initial sample is treated sequentially with the detergent, the chelating agent, the enzyme, and the fluorochrome in any sequence.

3. The method according to claim 1, wherein the initial sample is first treated with the chelating agent, then with the enzyme, then with the detergent, and then with the fluorochrome.

4. The method according to claim 1, wherein the initial sample is first treated with a combination of the chelating agent and the enzyme, then with the detergent, and then with the fluorochrome.

5. The method according to claim 1, wherein the initial sample is first treated with a combination of the chelating agent, the enzyme and the detergent, and then with the fluorochrome.

6. The method according to claim 1, wherein the initial sample is treated with a combination of the chelating agent, the enzyme, the detergent, and the fluorochrome.

7. The method according to claim 1 wherein the initial sample is incubated for at least 0.5 minutes at least in the treatment with the enzyme.

8. The method according to claim 7, wherein the incubation time is in the range of 0.5–20 minutes.

9. The method according to claim 1 wherein the temperature of the sample being treated is in the range of 15°–80° C. during at least the treatment with the enzyme.

10. The method according to claim 1 wherein the pH of the sample being treated is kept in the range of 6–11 by means of a buffer.

11. The method according to claim 10, wherein the buffer is selected from the group consisting of phosphate, sodium borate/HCl, glycine/NaOH, sodium borate/NaOH, barbital-Na/HCl, piperazine/HCl, tetraethylethylenediamine, trismaleate, dimethylaminoethylamine, triethanolamine/HCl, N-dimethylaminoleucylglycine/NaOH, tris/HCl, 2-amino-2-methylpropane-1,3-diol/HCl, and carbonate.

12. The method according to claim 11, wherein the chelating agent is a calcium-chelating agent.

13. The method according to claim 12, wherein the calcium-chelating agent is selected from the group consisting of EDTA, BAPTA, EGTA, APTRA, and DTPA.

14. The method according to claim 1, wherein the ion-chelating agent is used in a concentration of about at or below the concentration at which an increase of the concentration will result in a decrease of the stainability of *Pseudomonas fluorescens* in phosphate buffer, pH 7.4, with ethidium bromide in a concentration of 2 µg per ml in the presence of 0.05 vol/vol % Brij 96, as measured by flow cytometric fluorescence assessment.

15. The method according to claim 14, wherein the ion-chelating agent is used in a concentration of about 2–5 g per litre.

16. The method according to claim 1 wherein the proteolytic enzyme is selected from enzymes classified class 3.4 in the international enzyme nomenclature system of 1972, and enzymes of broad specificity classified in subclass 3.4.21.

17. The method according to claim 1, wherein the proteolytic enzyme has its maximum activity in the pH range of 6 to 11.

18. The method according to claim 16, wherein the proteolytic enzyme is subtilisin.

19. The method according to claim 1, wherein the enzyme is used in a concentration of at least 0.02 Anson unit.

20. The method according to claim 19, wherein the enzyme is used in a concentration of at least 0.05 Anson unit.

21. The method according to claim 20, wherein the enzyme is used in a concentration of about 0.05–0.5 Anson unit.

22. The method according to claim 21, wherein the enzyme is used in a concentration of about 0.08–0.15 Anson unit.

23. The method according to claim 1 wherein the detergent is a biological detergent.

24. The method according to claim 23, wherein the detergent is a nonionic biological detergent selected from the group consisting of a polyoxyethylene ether; a polyoxyethylene-sorbitan ester and digitonin.

25. The method according to claim 1, wherein the detergent is used in an amount of between 0.01 and 2 per cent by volume.

26. The method according to claim 25, wherein the detergent is used in an amount of 0.03–0.1 per cent by volume.

27. The method according to claim 1, wherein the fluorochrome is selected from DNA/RNA-binding fluorochromes, fluorochromes specifically binding to bacterial cell walls or bacterial flagella, and bacterial viability stains.

28. The method according to claim 27, wherein the fluorochrome is one which, when added in a concentration of 10 µg per ml at room temperature to unhomogenized whole milk having a fat content of 3.5% by weight, the resulting mixture being tumbled gently for 5 minutes, does not give rise to any staining of fat globules which is detectable by fluorescence microscopy on glass slides using a 50 watt mercury lamp as the radiation source.

29. The method according to claim 28, wherein the fluorochrome belongs structurally to the group of phenanthridium derived intercalators.

30. The method according to claim 29, wherein the fluorochrome is ethidium bromide.

31. The method according to claim 30, wherein the ethidium bromide is used in a concentration of at least 0.1 µg per ml of the liquid sample.

32. The method according to claim 31, wherein the ethidium bromide is used in a concentration of at least 0.5 µg per ml of the liquid sample.

33. The method according to claim 32, wherein the ethidium bromide is used in a concentration of about 1.5–10 µg per ml of the sample.

34. The method according to claim 1, wherein the initial sample is a sample of or derived from a food or a feed product.

35. The method according to claim 1, wherein the fat globules are milk fat globules.

36. The method according to claim 35, wherein the initial sample is a milk sample.

37. The method for the determination of the number of bacteria in an initial sample containing fat globules and somatic cells and/or protein particles, the method comprising subjecting the initial sample to a method according to claim 1 and subsequently irradiating the thus obtained conditioned sample or a part thereof with light in a wavelength range exciting the fluorochrome, assessing the fluorescence emitted, and determining the number of bacteria in the sample on the basis of the fluorescence.

38. The method according to claim 37, wherein substantially noremoval, dissolution or replacement of fat globules in the conditioned sample is performed prior to assessing the fluorescence emitted.

39. The method according to claim 37, wherein fat globules and solvent is at least partially removed and/or replaced and/or dissolved prior to assessing the fluorescence emitted.

40. The method according to claim 37, wherein the light exciting the fluorochrome is light from a broad band light source such as a xenon or mercury lamp.

41. The method according to claim 37, wherein the light exciting the fluorochrome is laser light.

42. The method according to claim 37, wherein the fluorescence is measured while the conditioned sample or part thereof is flowing as a liquid string in a flow cytometer.

43. The method according to claim 37, wherein the fluorescence is measured while the sample is applied as a film on the outer rim portion of a rotating disc.

44. The method according to claim 37, wherein the fluorescence is measured by epifluorescence microscopy.

45. The method according to claim 24, wherein the polyoxyethylene ether is selected from a lauryl ether, an oleyl ether, a stearyl ether, and a tridecyl ether.

46. The method according to claim 24, wherein the polyoxyethylenesorbitan ester is selected from monolaurate, monooleate, monopalmitate, monostearate, and trioleate.

47. The method according to claim 29, wherein the fluorochrome is selected from ethidium bromide and propidium iodide.

48. The method according to claim 16, wherein the enzyme classified in class 3.4 is selected from a subclass selected from 3.4.21 (enzymes of broad specificity), 3.4.22, 3.4.24, 3.4.99.

* * * * *

UNITED STATES PATENT AND TRADEMARK OFFICE
CERTIFICATE OF CORRECTION

PATENT NO. : 5,798,221
DATED : August 25, 1998
INVENTOR(S) : Poul Erik AEgidius

It is certified that error appears in the above-identified patent and that said Letters Patent is hereby corrected as shown below:

Claim 12.

The method according to claim [11] 1, wherein the chelating agent is a calcium-chelating agent.

Claim 38.

The method according to claim 37, wherein substantially [noremoval] no removal, dissolution or replacement of fat globules in the conditioned sample is performed prior to assessing the fluorescence emitted.

Signed and Sealed this

Twelfth Day of January, 1999

Attest:

Attesting Officer

*Acting Commissioner of Patents and Trademarks*